US008712792B2

(12) United States Patent
Bowman et al.

(10) Patent No.: US 8,712,792 B2
(45) Date of Patent: Apr. 29, 2014

(54) PERSONALIZED HEALTH COMMUNICATION SYSTEM

(75) Inventors: Bradley R Bowman, Tigard, OR (US); Philip D. Marshall, Portland, OR (US)

(73) Assignee: WebMD, LLC, New York, NY (US)

( * ) Notice: Subject to any disclaimer, the term of this patent is extended or adjusted under 35 U.S.C. 154(b) by 2139 days.

(21) Appl. No.: 10/624,098

(22) Filed: Jul. 21, 2003

(65) Prior Publication Data

US 2004/0019505 A1    Jan. 29, 2004

Related U.S. Application Data

(63) Continuation of application No. 09/511,963, filed on Feb. 24, 2000, now abandoned.

(51) Int. Cl.
*G06Q 50/22*    (2012.01)
*G06Q 50/24*    (2012.01)

(52) U.S. Cl.
USPC .................................................. 705/2; 705/3

(58) Field of Classification Search
None
See application file for complete search history.

(56) References Cited

U.S. PATENT DOCUMENTS

| | | | |
|---|---|---|---|
| 4,315,309 A | 2/1982 | Coli | 705/3 |
| 4,812,994 A | 3/1989 | Taylor et al. | 705/410 |
| 4,858,121 A | 8/1989 | Barber et al. | 705/2 |
| 4,868,376 A | 9/1989 | Lessin et al. | 235/492 |
| 4,882,474 A | 11/1989 | Anderl et al. | 235/380 |
| 4,916,611 A | 4/1990 | Doyle, Jr. et al. | 705/2 |
| 4,949,251 A | 8/1990 | Griffin et al. | 714/20 |
| 4,960,982 A | 10/1990 | Takahira | 235/382 |
| 4,984,272 A | 1/1991 | McIlroy et al. | 713/202 |
| 5,150,409 A | 9/1992 | Elsner | 713/177 |
| 5,241,671 A | 8/1993 | Reed et al. | 707/104.1 |
| 5,251,152 A | 10/1993 | Notess | 709/224 |
| 5,301,105 A | 4/1994 | Cummings, Jr. | 705/2 |
| 5,301,246 A | 4/1994 | Archibald et al. | 379/142.06 |
| 5,325,294 A | 6/1994 | Keene | 705/3 |
| 5,327,341 A | 7/1994 | Whalen et al. | 705/3 |
| 5,430,875 A | 7/1995 | Ma | 719/318 |
| 5,465,082 A | 11/1995 | Chaco | 340/825.49 |
| 5,491,800 A | 2/1996 | Goldsmith et al. | 709/221 |

(Continued)

OTHER PUBLICATIONS

PR Newswire. Aug. 23, 1999. WellMed, INc. "WellMed Introduces Industry's First Comprehensive Personal Health Management System Including Online Health Record".*

(Continued)

*Primary Examiner* — Robert Morgan
*Assistant Examiner* — Kristine Rapillo
(74) *Attorney, Agent, or Firm* — Wilmer Cutler Pickering Hale and Dorr LLP

(57) ABSTRACT

Personalization of access to health-related information on a computer network is provided based upon a health history of a user. In one implementation, personal health-related information about the user is obtaining from the user operating a client computer. The health-related information includes one or more health-related terms that each corresponds to a health-related concept. The health related terms provided by the user are correlated with a health terminology thesaurus that is stored on a computer-readable medium, such as at a server remote from the user client. Each of the health-related terms is associated with a single concept unique identifier that uniquely identifies a corresponding health-related concept. Health-related works or content is made accessible over the computer network by correlating the concept unique identifiers for the user's health information with corresponding concept unique identifiers that are associated with the health-related content.

20 Claims, 6 Drawing Sheets

(56) References Cited

U.S. PATENT DOCUMENTS

| | | | |
|---|---|---|---|
| 5,550,971 A | 8/1996 | Brunner et al. | 395/161 |
| 5,559,885 A | 9/1996 | Drexler et al. | 235/380 |
| 5,559,888 A | 9/1996 | Jain et al. | 380/25 |
| 5,560,008 A | 9/1996 | Johnson et al. | 713/201 |
| 5,572,422 A | 11/1996 | Nematbakhsh et al. | 705/3 |
| 5,588,148 A | 12/1996 | Landis et al. | 707/1 |
| 5,629,981 A | 5/1997 | Nerlikar | 713/168 |
| 5,664,109 A | 9/1997 | Johnson et al. | 705/2 |
| 5,664,207 A | 9/1997 | Crumpler et al. | 715/505 |
| 5,772,585 A | 6/1998 | Lavin et al. | 600/300 |
| 5,790,785 A | 8/1998 | Klug et al. | 713/202 |
| 5,809,476 A | 9/1998 | Ryan | 705/2 |
| 5,815,665 A | 9/1998 | Teper et al. | 709/229 |
| 5,827,180 A * | 10/1998 | Goodman | 600/300 |
| 5,832,488 A | 11/1998 | Eberhardt | 707/10 |
| 5,841,970 A | 11/1998 | Tabuki | 713/201 |
| 5,845,255 A | 12/1998 | Mayaud | 705/3 |
| 5,848,397 A | 12/1998 | Marsh et al. | 705/14 |
| 5,857,190 A | 1/1999 | Brown | 707/10 |
| 5,862,327 A | 1/1999 | Kwang et al. | 709/203 |
| 5,867,821 A | 2/1999 | Ballantyne et al. | 705/2 |
| 5,903,889 A | 5/1999 | De la Huerga et al. | 707/3 |
| 5,905,884 A | 5/1999 | Williams | 709/227 |
| 5,915,240 A | 6/1999 | Karpf | 705/2 |
| 5,953,704 A | 9/1999 | McIlroy et al. | 705/2 |
| 5,960,403 A * | 9/1999 | Brown | 705/2 |
| 5,966,715 A | 10/1999 | Sweeney et al. | 707/203 |
| 5,967,789 A | 10/1999 | Segel et al. | 434/236 |
| 5,974,412 A | 10/1999 | Hazlehurst et al. | 707/3 |
| 5,978,842 A | 11/1999 | Noble et al. | 709/218 |
| 6,006,269 A | 12/1999 | Phaal | 709/227 |
| 6,018,619 A | 1/2000 | Allard et al. | 709/224 |
| 6,031,818 A | 2/2000 | Lo et al. | 370/216 |
| 6,070,160 A | 5/2000 | Geary | 707/4 |
| 6,073,106 A | 6/2000 | Rozen et al. | 705/3 |
| 6,073,163 A | 6/2000 | Clark et al. | 709/203 |
| 6,092,196 A | 7/2000 | Reiche | 713/200 |
| 6,112,183 A | 8/2000 | Swanson et al. | 705/2 |
| 6,141,759 A | 10/2000 | Braddy | 713/201 |
| 6,167,523 A | 12/2000 | Strong | 713/201 |
| 6,178,416 B1 | 1/2001 | Thompson et al. | 707/3 |
| 6,189,036 B1 | 2/2001 | Kao | 709/229 |
| 6,253,228 B1 | 6/2001 | Ferris et al. | 709/203 |
| 6,263,330 B1 | 7/2001 | Bessette | 707/4 |
| 6,292,796 B1 | 9/2001 | Drucker et al. | 707/4 |
| 6,334,778 B1 * | 1/2002 | Brown | 434/258 |
| 6,347,374 B1 | 2/2002 | Drake et al. | 713/200 |
| 6,362,836 B1 | 3/2002 | Shaw et al. | 345/744 |
| 6,385,611 B1 | 5/2002 | Cardona | 707/6 |
| 6,401,072 B1 | 6/2002 | Haudenschild et al. | 705/3 |
| 6,449,598 B1 | 9/2002 | Green et al. | 705/2 |
| 6,826,696 B1 | 11/2004 | Chawla et al. | 713/201 |

OTHER PUBLICATIONS

Press Release. Feb. 22, 1999. Apelon, Inc. "WellMed and Lexical Technology Announce Joint Development Agreement for Online Consumer Health Records".*

"WellMed Introduces Industry's First Comprehensive Personal Health Management System Including Online Health Record" Aug. 23, 1999, PR Newswire.

* cited by examiner

Fig. 4

```
Personal Health Message Receiving User Interface          130

General      132            View Messages     134
      _ Allow all messages        x Personal Health Home Page
      _ Block all messages        _ E-Mail Custom       136
      x Allow messages that match the following characteristics Gender:  x Males   _ Females   _ Both    140

Age:    Greater than 40   Less than 60    142

General
      _ Pregnant          144          _ Diabetes Type I
      _ High Blood Pressure            _ Diabetes Type II
      _ Elevated Cholesterol           _ Breast Cancer
      _ Heart Disease                  _ Prosate Cancer
                                       _ Colon Cancer Groups
      _ Smokers           146          _ Non-Smokers
      _ Exercisers                     _ Non-exercisers
      _ Underweight                    _ Overweight Other:             148
    ┌─────────────────────────┐       ┌──────────┐
    │ sarcoidosis             │       │ FIND/ADD │
    └─────────────────────────┘       └──────────┘
    Criteria Preview Window
    ┌─────────────────────────┐                    152
    │ Males                   │                 ┌──────┐
    │ Age 40 - 60             │                 │ POST │
    │ Sarcoidosis             │                 └──────┘
    │                         │
    │              150        │
    └─────────────────────────┘
```

Fig. 5

Personal Health Message Transmitting User Interface 160

Gender: x Males _ Females _ Both  166

Age: Greater than 40  Less than 60  168

General  170
_ Pregnant
_ High Blood Pressure
_ Elevated Cholesterol
_ Heart Disease _ Diabetes Type I
_ Diabetes Type II
_ Breast Cancer
_ Prosate Cancer
_ Colon Cancer Groups
_ Smokers  172
_ Exercisers
_ Underweight _ Non-Smokers
_ Non-exercisers
_ Overweight Other:  174

| sarcoidosis | FIND/ADD |

Criteria Preview Window

| Males<br>Age 40 - 60  180<br>Sarcoidosis | POST  182 |

Title: | Just diagnosed with sarcoidosis |  176

Message:

| I've just been diagnosed with sarcoidosis. How can I expect it to affect me and my family?<br><br>176 |

PERSONALIZED HEALTH COMMUNICATION SYSTEM

This application is a continuation of United States patent application Ser. No. 09/511,963, filed Feb. 24, 2000, entitled PERSONALIZED HEALTH COMMUNICATION SYSTEM, which is hereby incorporated by reference in its entirety for each of its teachings and embodiments.

FIELD OF THE INVENTION

The present invention relates to providing communication over a computer network and, in particular, to providing personalized communication between users according to personal health information about them.

BACKGROUND AND SUMMARY OF THE INVENTION

Consumer health information is growing in importance and popularity, with computer networks such as the Internet providing a growing share of the information. It is estimated that health issues are addressed at tens of thousands of online sites with potentially millions of pages of health-related works or content. With a general lack of clinical and editorial standards for health-related content, lay consumers without specific medical training, and even trained medical professionals, can have relatively little success in finding desired or relevant information among such vast resources.

Moreover, given the extremely personal nature of health, most individuals have minimal interest in browsing materials that have no relevance to their health or the health of their families. Yet most of the health information available at conventional network (e.g., Internet) sites or portals addresses only general topics. Such information seldom has any particular relevance to individual users. Accordingly, there is a need for an improved way of obtaining relevant health-related information over computer networks such as the Internet.

Much of the health information that is available is generally clinical information about the health conditions. In many instances, however, such clinical information does not fully convey the effects and consequences of some health conditions, particularly for lay individuals without medical training. Accordingly, many people would be interested in discussing their health conditions with other people that have those conditions. For people having both common and uncommon health conditions, the ability to discuss the condition with others who are in similar circumstances can provide levels of understanding and information that are not otherwise readily available. However, health privacy prevents many such people from contacting each other. Also, some health conditions are relative uncommon, which can further complicate the ability of people with similar health conditions to identify and to contact each other.

The present invention provides systems, methods, and computer software by which multiple users at network-connected computers establish communication with each other according to personal health history information. Each user typically is a lay individual without specific medical training. The computer network may be private or public and may be a local area network or a wide area network. For example, the computer network may include the Internet.

In one implementation, each of multiple users provides personal health history information over the Internet to a personalized health communication system. The personal health information may, relate to a variety of personal and health conditions, which may include medical diagnoses like diabetes, high blood pressure, pneumonia, or pregnancy, or any current or past health problem like poor vision, chronic joint pain, cancer, or alcoholism, etc., and other health and personal information.

At least one user defines personal health message receiving criteria for determining messages to be received from other users who meet the personal health message receiving criteria. With regard to the personal health message receiving criteria, the user is referred to as a message receiving user. The personal health message receiving criteria are stored on a computer in association with identifying information for the message receiving user. The personal health message receiving criteria include typically plural personal health-related factors that are included in the personal health information collected about the user. The personal health message receiving criteria indicate combinations of personal health characteristics about which the user is willing to communicate with other users.

At least one user defines personal health message transmitting criteria for directing a selected message to other users whose personal health message receiving criteria match the personal health message transmitting criteria. With regard to the personal health message transmitting criteria, the user is referred to as a message transmitting user. The personal health message transmitting criteria are stored on a computer in association with identifying information for the message transmitting user.

The personal health message transmitting criteria include typically plural personal health-related factors that are included in the personal health information collected about each user. The personal health message transmitting criteria represent characteristics of a message receiving user with whom the message transmitting user would like to communicate. The message transmitting user also submits a message (e.g., an e-mail message) for transmission to message receiving users with personal health message receiving criteria that conform to the personal health message transmitting criteria.

The message receiving users with personal health message receiving criteria that conform to the personal health message transmitting criteria are then identified, and the message of the message transmitting user is transmitted to the message receiving user. In one implementation, the personal health communication system maintains in confidence the identity and personal health history of both the transmitting and receiving users.

The present invention provides communication between users, commonly lay users without specific medical training, based upon the personal health characteristics of the users. The identity and personal health information of the users are maintained in confidence. As a result, people with shared health conditions may communicate with each other to exchange information about their health conditions, how those conditions affect their lives and which treatments and therapies have been most effective in treating their condition or symptoms of their illness.

Additional objects and advantages of the present invention will be apparent from the detailed description of the preferred embodiment thereof, which proceeds with reference to the accompanying drawings.

BRIEF DESCRIPTION OF THE DRAWINGS

FIG. 4 is a diagrammatic illustration of a personal health message receiving user interface that is rendered on a user client computer display screen;

FIG. 5 is a diagrammatic illustration of a personal health message transmitting user interface that is rendered on a user client computer display screen.

DETAILED DESCRIPTION OF PREFERRED EMBODIMENTS

Figure 1:
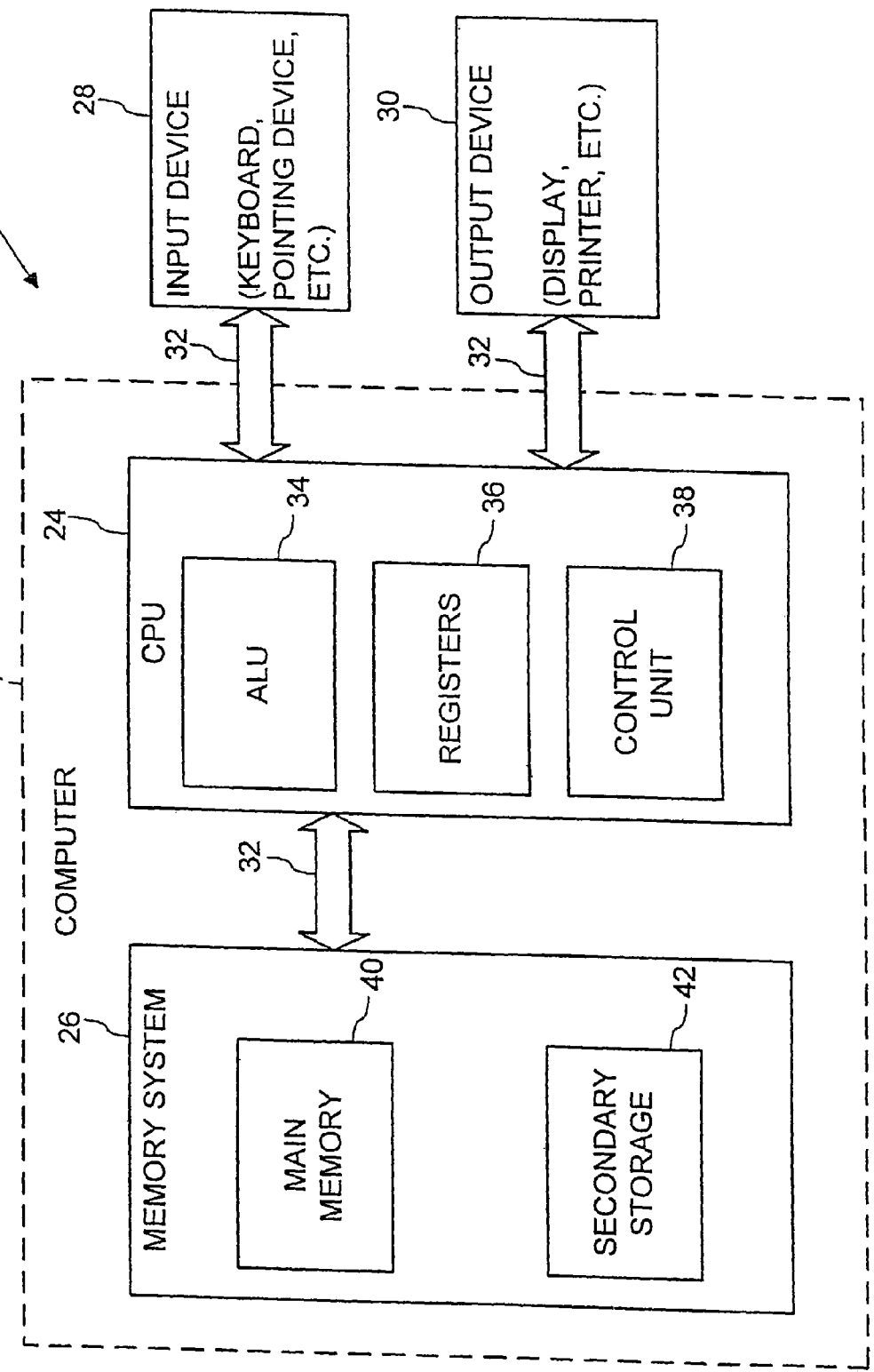
FIG. 1 is a block diagram of a computer system that may be used to implement the present invention.

FIG. 1 illustrates an operating environment for an embodiment of the present invention as a computer system 20 with a computer 22 that comprises at least one high speed processing unit (CPU) 24 in conjunction with a memory system 26, an input device 28, and an output device 30. These elements are interconnected by at least one bus structure 32.

The illustrated CPU 24 is of familiar design and includes an ALU 34 for performing computations, a collection of registers 36 for temporary storage of data and instructions, and a control unit 38 for controlling operation of the system 20. The CPU 24 may be a processor having any off a variety of architectures including Alpha from Digital, MIPS from MIPS Technology, NEC, IDT, Siemens, and others, x86 from Intel and others, including Cyrix, AMD, and Nexgen, and the PowerPC from IBM and Motorola.

The memory system 26 generally includes high-speed main memory 40 in the form of a medium such as random access memory (RAM) and read only memory (ROM) semiconductor devices, and secondary storage 42 in the form of long term storage mediums such as floppy disks, hard disks, tape, CD-ROM, flash memory, etc., and other devices that store data using electrical, magnetic, optical or other recording media. The main memory 40 also can include video display memory for displaying images through a display device. Those skilled in the art will recognize that the memory 26 can comprise a variety of alternative components having a variety of storage capacities.

The input and output devices 28 and 30 also are familiar. The input device 28 can comprise a keyboard, a mouse, a physical transducer (e.g., a microphone), etc. The output device 30 can comprise a display, a printer, a transducer (e.g., a speaker), etc. Some devices, such as a network interface or a modem, can be used as input and/or output devices.

As is familiar to those skilled in the art, the computer system 20 further includes an operating system and at least one application program. The operating system is the set of software which controls the computer system's operation and the allocation of resources. The application program is the set of software that performs a task desired by the user, using computer resources made available through the operating system. Both are resident in the illustrated memory system 26.

In accordance with the practices of persons skilled in the art of computer programming, the present invention is described below with reference to acts and symbolic representations of operations that are performed by computer system 20, unless indicated otherwise. Such acts and operations are sometimes referred to as being computer-executed and may be associated with the operating system or the application program as appropriate. It will be appreciated that the acts and symbolically represented operations include the manipulation by the CPU 24 of electrical signals representing data bits which causes a resulting transformation or reduction of the electrical signal representation, and the maintenance of data bits at memory locations in memory system 26 to thereby reconfigure or otherwise alter the computer system's operation, as well as other processing of signals. The memory locations where data bits are maintained are physical locations that have particular electrical, magnetic, or optical properties corresponding to the data bits.

Figure 2:
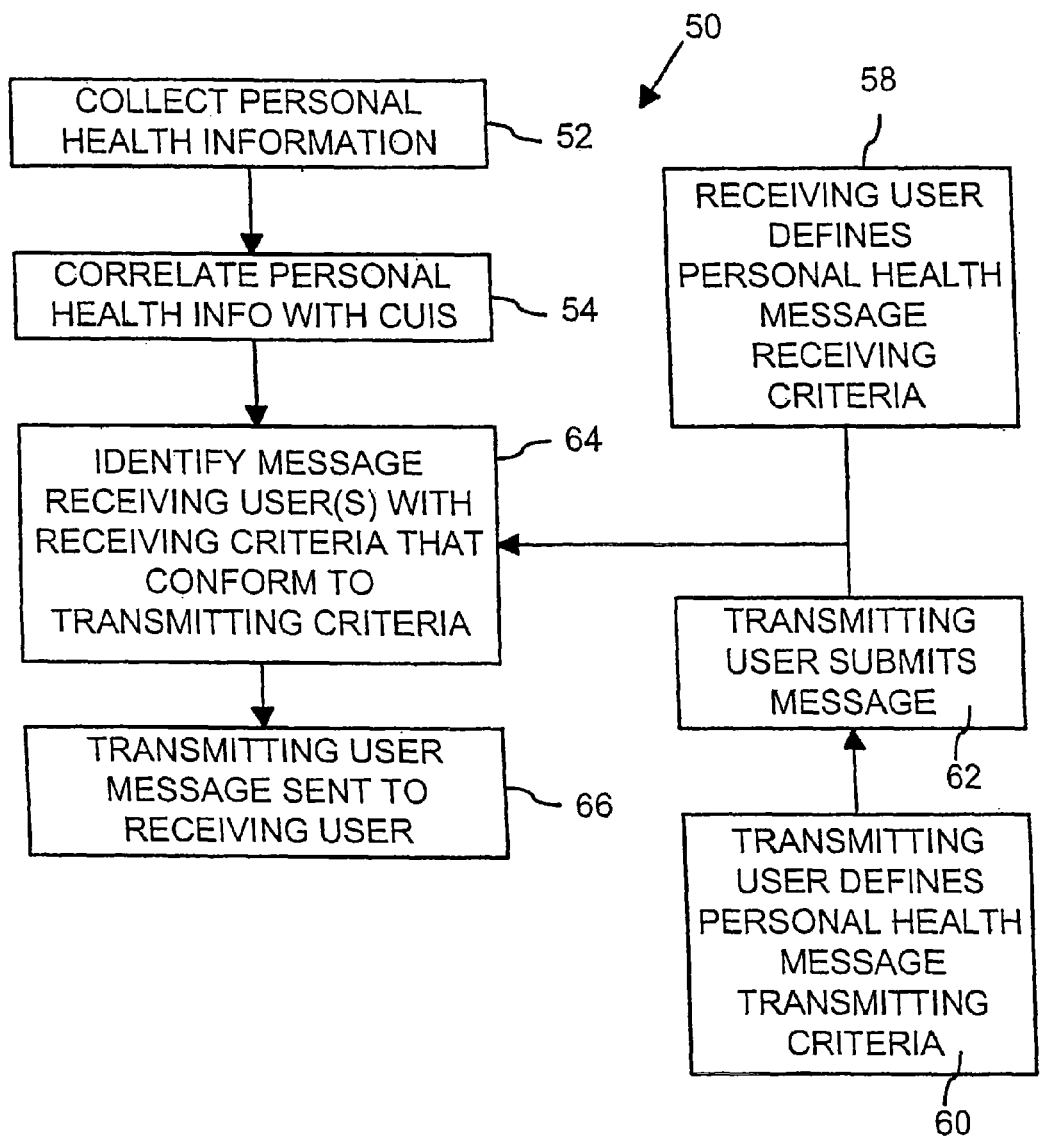
FIG. 2 is a flow-diagram of a personalized health communication process by which multiple users at network-connected computers communicate with each other according to personal health history information.

FIG. 2 is a flow diagram of a personalized health communication process 50 by which multiple users at network-connected computers communicate with each other according to personal health history information. Each user typically is a lay individual without specific medical training. The computer network may be private or public and may be a local area network or a wide area network. In one implementation, each user utilizes personalized health communication process 50 and provides personal health history information over the Internet.

Process block 52 indicates that personal health information is collected about each user. The personal health information may relate to health conditions, which may include medical diagnoses like diabetes, high blood pressure, pneumonia, or pregnancy, or any current or past health problem like poor vision, chronic joint pain, cancer, or alcoholism.

In addition, the health information could relate to allergies, tests, vaccinations, surgeries or procedures, etc. that affect or have affected the health of the user or that are a part of the user's health history.

For purposes of explanation, the following description is made with reference to the health information relating to health conditions. It will be appreciated that the description is similarly applicable to other types of health information, including information relating to allergies, tests, vaccinations, surgeries or procedures, etc.

Process block 54 indicates that the personal health information for each user are correlated with predefined concept unique identifiers (CUIs). Each concept unique identifier uniquely identifies a predefined health-related concept (e.g., a health condition). The concept unique identifiers provide standardized identification of the predefined health-related concepts independent of traditional variations between lay medical and clinical medical terminology for health conditions, as described below in greater detail. In one implementation, the concept unique identifiers are in the form of alphanumeric segments (e.g., 8 characters each). Alternatively, numeric or alphabetic segments could be used.

The concept unique identifiers are based on core medical concepts, enabling multiple synonyms and related terms to be mapped to the same concept unique identifier or code. For example, "hyperpeisis," "elevated systolic pressure," "high blood pressure," "hypertensive vascular disease" and "high blood" are all used in consumer and professional circles to describe the same thing: high blood pressure. Accordingly, all these terms would be mapped or associated with a single concept unique identifier.

Process block 58 indicates that at least one user defines personal health message receiving criteria for determining messages to be received from other users who meet the personal health message receiving criteria. With regard to the personal health message receiving criteria, the user is referred to as a message receiving user. The personal health message receiving criteria are stored on a computer in association with identifying information for the message receiving user.

The personal health message receiving criteria include typically plural personal health-related factors that are included in the personal health information collected about each user. For example, the personal health message receiving criteria may include one or more personal characteristics such as gender, age or age ranges, smoking or non-smoking habits, exercising or non-exercising habits, or being overweight or underweight; predefined health conditions such as being pregnant, or having high blood pressure, elevated cholesterol, heart disease, diabetes (Type I or II), breast cancer, prostate cancer, colon cancer, etc.; and user-defined health conditions that the user enters or indicates by name. Each of the personal health message receiving criteria, including personal characteristics, predefined health conditions, and user-defined health conditions, is correlated with a corresponding concept unique identifier.

The personal health message receiving criteria indicate combinations of personal health characteristics about which the user is willing to communicate with other users. For people having both common and uncommon health conditions, the ability to discuss the condition with others who have the condition and are in similar circumstances can provide levels of understanding and information that are not otherwise readily available.

Process block 60 indicates that at least one user defines personal health message transmitting criteria for directing a selected message to other users whose personal health message receiving criteria match the personal health message transmitting criteria. With regard to the personal health message transmitting criteria, the user is referred to as a message transmitting user. The personal health message transmitting criteria are stored on a computer in association with identifying information for the message transmitting user.

The personal health message transmitting criteria include typically plural personal health-related factors that are included in the personal health information collected about each user. For example, the personal health message transmitting criteria may include one or more personal characteristics, predefined health conditions, and user-defined health conditions, as described above with reference to process block 58. Each of the personal health message transmitting criteria is correlated with a corresponding, concept unique identifier. The personal health message transmitting criteria represent characteristics of a message receiving user with whom the message transmitting user would like to communicate.

Process block 62 indicates that the message transmitting user submits a message (e.g., an e-mail or network communication channel) for transmission to message receiving users with personal health message receiving criteria that conform to the personal health message transmitting criteria. The message may include, for example, a statement of one or more specific health conditions and a question about treatments, consequences, etc. concerning the conditions.

As an example, Joe is a 47 year old male who consults his physician because of a chronic cough. After an examination and chest x-ray his physician diagnoses his condition as sarcoidosis. Joe's physician informs him that this is an incurable condition, without a known cause, which affects about 40 out of every 100,000 individuals. He goes on to provide Joe with some information about sarcoidosis and recommends treatment with Prednisone, a steroid medication. In this example, Joe leaves the office with a diagnosis and some information, but he now wishes to talk to someone else with sarcoidosis—preferably someone like himself. So in accordance with personalized health communication process 50, Joe defines personal health message transmitting criteria indicating male, between ages 40 and 60, and sarcoidosis, and composes a message stating: "I was just diagnosed with sarcoidosis. How is this really going to affect me and my family?"

Process block 64 indicates that message receiving users with personal health message receiving criteria that conform to the personal health (message transmitting criteria are identified. Generally, the message transmitting criteria represent cumulative or conjunctive conditions. The message receiving criteria of a message receiving user conform to message transmitting criteria when the message receiving criteria match each of the specified message transmitting criteria. In the illustrated example, the message transmitting criteria are male, between ages 40 and 60, and sarcoidosis, and the message receiving criteria of a message receiving user conform to message transmitting criteria when the message receiving criteria designate each of the message transmitting criteria. In other implementations, the message receiving criteria of a message receiving user may also conform to message transmitting criteria when the message receiving criteria match some or most of the specified message transmitting criteria (e.g., at least the user-defined health conditions).

Process block 66 indicates that the message of the message transmitting user is transmitted to the message receiving user. In one implementation, the message is transmitted to the message receiving user without identifying the message receiving user to the message transmitting user. The message may be transmitted as a standard e-mail message to an address that is predefined by the message receiving user or may be transmitted as a message within a computer system that performs personalized health communication process 50. Upon receipt of the message, the message receiving user may choose to reply to the message transmitting user, such as by a reply e-mail message to an e-mail address included in the transmitted message.

Exemplary concept unique identifiers and corresponding predefined health-related concepts or terms for several health conditions are listed below in Table 1. The relationship between each concept unique identifier and the corresponding health-related term or terms forms a data structure that is stored in a computer-readable medium and includes a concept unique identifier (e.g., alphanumeric) and one or more associated health-related terms. The data structure allows uniform identification of health-related concepts despite a variety of lay medical terms and clinical medical terms being in use. The listing of Table 1 is not exhaustive of the health condition medical terms to which the concept unique identifiers may be applied.

TABLE 1

| Clinical Medical Term or Terms | Lay Medical Term | CUI |
| --- | --- | --- |
| guarding of the abdomen-involuntary | abdomen sensitive to touch | C0238547 |
| nipple discharge, abnormal | abnormal nipple discharge | C0149741 |
| acid stomach | acidy stomach | C0013395 |
| Addison's/Adrenal Disease | Addison's Disease | C0001403 |
| adrenalin-test | adrenalin level | C0201998 |
| aminophylline, serum | aminophylline level | C0002575 |
| amitriptyline, serum | amitriptyline level | C0202316 |

TABLE 1-continued

| Clinical Medical Term or Terms | Lay Medical Term | CUI |
|---|---|---|
| ammonia - test | ammonia level | C0201879 |
| Death Adder Antivenom | Antivenom | C00034.50 |
| radial nerve disorder | arm nerve problem | C0434268 |
| salicylate, serum | aspirin level | C0202463 |
| AST (Aspartate Aminotransferase) | AST | C0004002 |
| Autism/Asperger | autism | C0004352 |
| congenital band syndrome | baby bands | C0220724 |
| urination, bed wetting | bed wetting | C0014394 |
| honeybee desensitization injection | bee desensitization injections | C0474187 |
| oropharynx lesion biopsy | biopsy of throat | C0192211 |
| Interstitial Cystitis, see Urinary Tract Infections | Bladder Infection | C0010692 |
| Landmine Survivors | Blast injury from explosion | C0413283 |
| periods, menstrual - bleeding between | bleeding between menstrual periods | C0302811 |
| ear discharges/bleeding | bleeding from ear | C0271412 |
| HCG (qualitative - serum) | blood HCG level | C0430064 |
| hemoglobin; serum | blood hemoglobin level | C0523685 |
| semen - bloody | blood in my semen | C0235756 |
| lead - serum | blood lead level | C0524167 |
| lithium, serum | blood lithium level | C0337452 |
| hypornagnesemia test | blood magnesium test | C0202125 |
| hypokalemia test | blood potassium test | C0202194 |
| Total Blood Protein | blood protein measurement | C0201838 |
| herpes culture | blood test for herpes simplex | C0201341 |
| liver disease test panel - autoimmune | blood tests for liver disease | C0023901 |
| No System | Body as a Whole | C0229960 |
| nonunion | bone nonunion | C0016665 |
| born with an optic disc abnormality | born with an abnormal optic nerve | C0521571 |
| gastric culture | breath test for ulcer disease (h. pylori) | C0458053 |
| increased rate of breathing | breathing fast | C0231835 |
| backbone fracture | broken back | C0080179 |
| reduction of broken bone | broken bone put back in place | C0161946 |
| metacarpal fracture | broken metacarpal | C0272677 |
| sacrum/coccyx fracture | broken tailbone | C0149860 |
| stool *C. difficile* toxin | c dif culture | C0201112 |
| monoplegia of upper extremity | can't move arm | C0154703 |
| monoplegia of lower extremity | can't move leg | C0154702 |
| urine s.g. | can't pee | C0028961 |
| vision, night blindness | can't see at night | C0028077 |
| inability to sleep | can't sleep | C0021603 |
| smell, impaired | can't smell | C0481703 |
| carpel tunnel biopsy | carpal tunnel surgery | C0196576 |
| hoarseness or changing voice | changing voice | C0518179 |
| chest laceration | chest cut | C0432951 |
| Hiccups, Chronic | chronic hiccups | C0019,521 |
| chronic pain and fatigue condition | chronic pain | C0150055 |
| prochlorperazine injection | compazine injection | C0033231 |
| wound complications after c section | complications after c section | C026.9815 |
| Crying Baby | Constantly crying baby | C0424961 |
| Corpus Callosum, Age | Corpus Callosum | C0010090 |
| hydroxyzine injection | cortisone shot | C1101137 |
| Creatinine and Creatinine Clearance | Creatinine Clearance | C0373595 |
| orbit CT scan | CT of eye socket | C0202754 |
| CXR | CXR | C0202783 |
| Cymba concha of auricle | Cymba concha | C022931f |
| sweat electrolytes | Cystic fibrosis test | C0428295 |
| Ear Infections (Otitis Media) | | C0699744 |
| ear laceration | | C0561238 |
| ear noise/buzzing | | C0235283 |
| ear test | | C0004286 |
| Ear, Patella, Short Stature Syndrome | | C0347915 |
| Earwax | | C0007844 |
| earwax problems | | C0007844 |
| Eastern Medicine | | C0025123 |
| eat fatty foods | | C0521974 |
| Eating Disorders, Anorexia Nervosa | | C0003125 |
| Eating Disorders, Bulimia Nervosa | | C0376289 |
| eating, excessive indulgence | | C0020505 |
| ebola virus infection | | C0013480 |
| EBV antibodies | | C0236525 |
| Eccrine sweat gland | | C0013492 |
| ECF | | C0037265 |
| ECG - exercise treadmill test | | C0430507 |
| echocardiogram - transesophageal | | C0206054 |
| Echocardiogram (Cardiac Echo) | | C0013516 |
| edema In pregnancy | | C0085649 |
| edrophonium test | | C0204045 |
| effects of child abuse | | C0562381 |
| effects of domestic violence | | C0562381 |

TABLE 1-continued

| Clinical Medical Term or Terms | Lay Medical Term | CUI |
| --- | --- | --- |
| effects of elder abuse | | C0562381 |
| effects of spouse abuse | | C0562381 |
| EGD (esophagogastroduodenoscopy) | | C0079304 |
| Elastosis Dystrophica | | C0033847 |
| elbow cast | | C0371328 |
| elbow joint fluid | | C0263962 |
| elbow problems | | C0231659 |
| elbow surgery | | C0407839 |
| elbow swelling | | C0575641 |
| elder abuse victim | | C0013772 |
| Electrocardiogram (ECG, EKG) | | C0013798 |
| Electronic Fetal Monitoring (EFM) | | C0015945 |
| elevated PSA | | C0262466 |
| endocervix cancer | | C0007847 |
| Endocrine and Glandular Conditions | | C0014130 |
| endocrine anomaly | | C0014130 |
| enlarged kidney from urinary obstruction | | C0020295 |
| enlarged liver | | C0019209 |
| enlargement of one pupil | | C0003078 |
| Entamoeba dispar | | C0014321 |
| entercysis | | CS019742 |
| Enterovirus infection (Non-Polio) | | C0014378 |
| enzyme assay | | C0555153 |
| Eosinophilia Myalgia | | C0085179 |
| Epigastric area | | C0521440 |
| epiglottis Cancer | | C0014540 |
| Epilepsy/Convulsive Disorders | | C0014544 |
| epine shrine injection | | C0029191 |
| Epstein-Barr virus test | | C0201373 |
| Erection Problems | | C0455842 |
| Erythrokeratodermia with Ataxia | | CS020602 |
| erythropoietin injection. | | C0306097 |
| esophageal function studies | | C0700223 |
| Esophagus condition | | C0014852 |
| esophogus narrowing | | C0014866 |
| Ethmoidal sinus | | C0153477 |
| excess female body hair | | C0019572 |
| excessive hunger | | C0020175 |
| excessive vomiting | | C0042963 |
| Excretory Urography | | C0042070 |
| Exercise and Fitness | | C0015259 |
| exercise electrocardiography | | C0015260 |
| exercise treadmill ECG | | C0015260 |
| Exomphalos-Macroglossia-Gigantism | | C0004903 |
| exposure illness | | C0020672 |
| Exposure to Sexually Transmitted Diseases | | C0262661 |

The concept unique identifiers and corresponding predefined health-related terms form a health terminology thesaurus that is stored on a computer-readable medium and provides the concept unique identifiers based upon the health-related terms. In one implementation, the health terminology thesaurus incorporates terminology from many health-related vocabularies, including The Systematized Nomenclature of Medicine (SNOMED) promulgated by the College of American Pathologists and the International Classification of Diseases: 9th. revision, Clinical Modification, promulgated by the Health Care Financing Administration, as well as many other vocabularies and consumer and lay medical terms. The thesaurus of one implementation is an extension of the Unified Medical Language System (UMLS) Metathesaurus promulgated by the National Library of Medicine.

Figure 3:
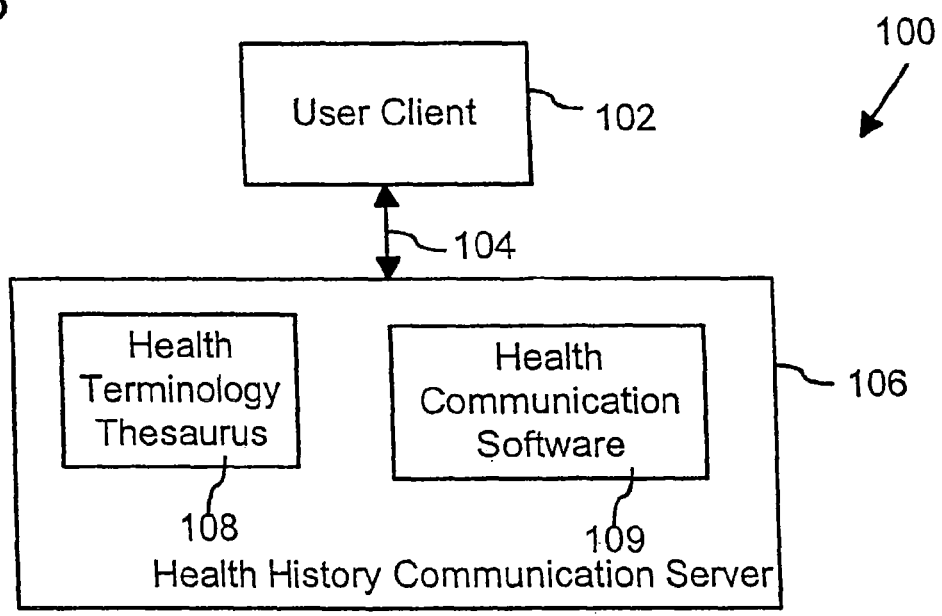
FIG. 3 is a block diagram of one implementation of a personalized health communication computer system.

FIG. 3 is a block diagram of one implementation of a personalized health communication computer system 100, which includes for each user a user client 102 (only one shown) that communicates over a computer network 104 with a personalized health communication server 106. Server 106 may be implemented as one or more server computers. In the case of multiple server computers, they may be local to each other or may be remote from each other and in communication via a computer network. User client 102 may be implemented as, for example, an interactive document or page that is accessible by the user at a client computer with conventional browser software.

Personalized health communication server 106 stores a health terminology thesaurus 108 that correlates health terminology submitted as user-defined health conditions with concept unique identifiers. Personalized health communication server 106 also includes health communication software 109 that cooperates with user client 102 for identifying and transmitting messages to receiving users with personal health message receiving criteria that conform to personal health message transmitting criteria of transmitting users.

FIG. 4 is a diagrammatic illustration of a personal health message receiving user interface 130 that is rendered on a display screen of a user client 102. Personal health message receiving user interface 130 assists a user in providing personal health information to personalized health communication computer system 100.

User interface 130 includes general message receiving controls 132 by which the message receiving user can choose generally to receive or to block all messages. A view messages control 134 allows the message receiving user to select how personal health messages are to be received, such as at a designated personal health communication homepage (e.g., FIG. 6), at a designated email address, or both. A custom message receiving control 136 allows the user to elect to receive messages according to customized personal health message receiving criteria that are indicated by the custom controls. Custom message receiving control 136 includes gender controls 140, age controls 142, predefined conditions controls 144, general characteristics controls 146, and user-defined health conditions input control 148 for defining the message receiving criteria.

In the illustrated implementation, gender controls 140, predefined conditions controls 144, and general characteristics controls 146 list specific characteristics or fields that are selectable by checkboxes, for example, or other selectable graphics controls. Age controls 142 are illustrated as numeric fields in which users may enter arbitrary numeric values. User-defined conditions input control 148 cooperates with health terminology thesaurus 108 and health communication software 109 to identify the terms for user-defined conditions in health terminology thesaurus 108. The message receiving criteria, including any unidentified terms that the user elects to add to the thesaurus, are listed in a criteria preview window 150. Concept unique identifiers are correlated with the conditions indicated by predefined conditions controls 146, general characteristics controls 146, and user-defined conditions input control 148, which conditions are summarized in criteria preview window 150. The message receiving criteria indicated by the custom controls are transmitted to server 106 in response to user activation of a post criteria control 152.

FIG. 5 is a diagrammatic illustration of a personal health message transmitting user interface 160 that is rendered on a display screen of a user client 102. Personal health message transmitting user interface 160 assists a user in providing personal health information to personalized health communication computer system 100.

User interface 160 includes a custom message transmitting control 162 that allows the user to define the message transmitting criteria according to which messages are transmitted to receiving users. Message transmitting control 162 includes gender controls 166, age controls 168, predefined conditions controls 170, general characteristics controls 172, and user-defined health conditions input control 174. A user composes a message in a message pane 176, and composes a message title in a message title pane 178.

In the illustrated implementation, gender controls 166, predefined conditions controls 170, and general characteristics controls 172 list specific characteristics or fields that are selectable by checkboxes, for example, or other selectable graphics controls. Age controls 168 are illustrated as numeric fields in which, users may enter arbitrary numeric values. User-defined conditions input control 174 cooperates with health terminology thesaurus 108 and health communication software 109 to identify the terms for user-defined conditions in health terminology thesaurus 108.

The message transmitting criteria, including any unidentified terms that the user elects to add to the thesaurus, are listed in a criteria preview window 180. Concept unique identifiers are correlated with the conditions indicated by predefined conditions controls 170, general characteristics controls 172, and user-defined conditions input control 174, which conditions are summarized in criteria preview window 180. The message and the message transmitting criteria indicated by the custom controls are transmitted to server 106 in response to user activation of a post message control 182.

In an optional implementation, health communication personalization software 109 further includes a health terminology spell checking component that checks the spelling of terms entered by users into user-defined conditions input control 148 and user-defined conditions input control 174. In the event of apparent misspellings or unrecognized terms, server 106 returns one or more suggested correct spellings.

Figure 6:
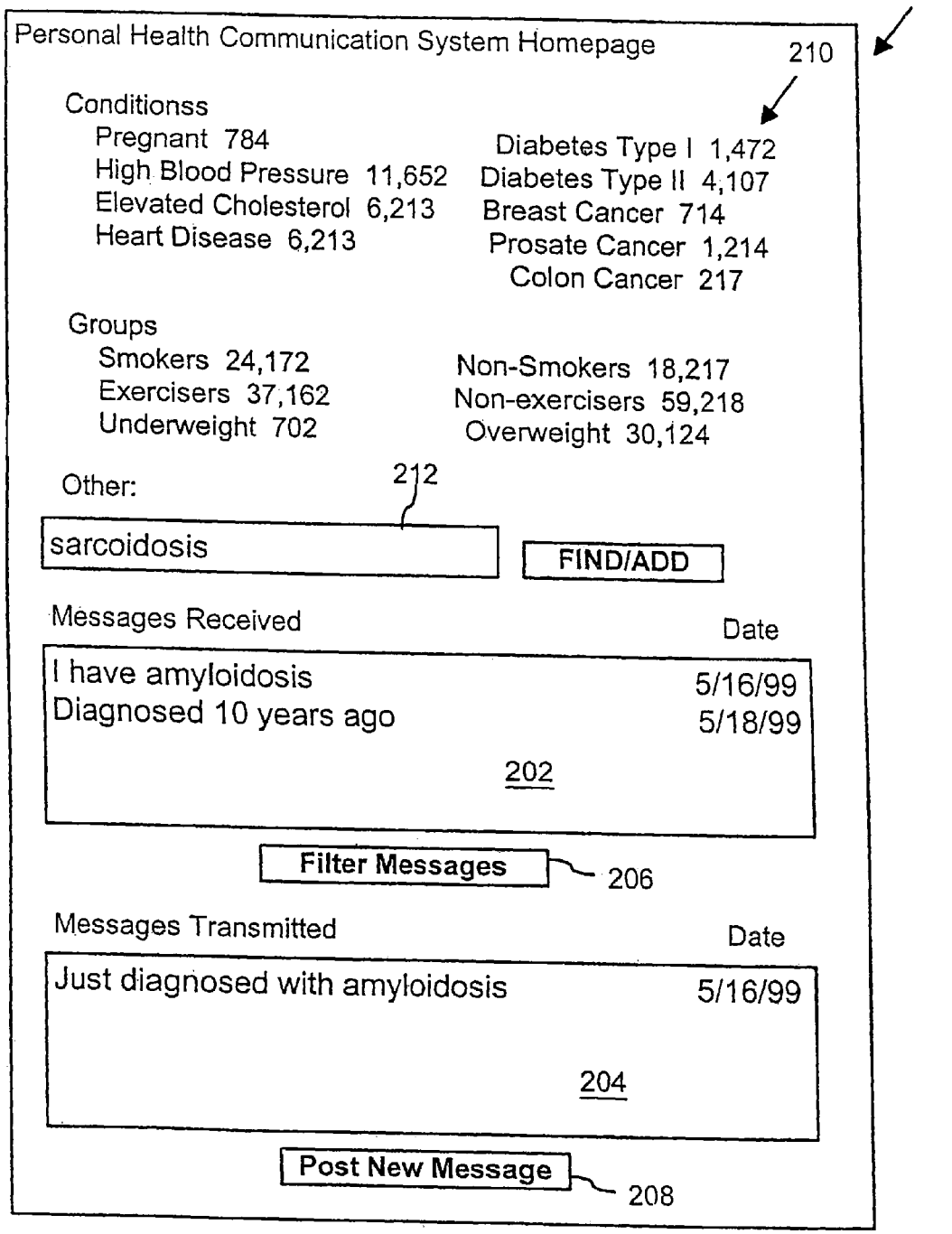
FIG. 6 is a diagrammatic illustration of a personal health communication user interface that is rendered on a user client computer display screen.

As described above with reference to process block 66, the message of the message transmitting user may be transmitted as a standard e-mail message to an address that is predefined by the message receiving user or may be transmitted as a message within a computer system that performs personalized health communication process 50. FIG. 6 is a diagrammatic illustration of a personal health communication user interface 200 that is rendered on a display screen for the user by user client 102. Personal health communication user interface 200 assists a user in managing messages and provides general information about users of personalized health communication process 50 or personalized health communication computer system 100.

User interface 200 includes a received messages pane 202 and a transmitted messages pane 204 that respectively indicate messages that are received and transmitted by a user based on personal health history information. Received messages pane 202 and transmitted messages pane 204 may indicate messages in a variety of ways, but are shown listing message titles and the dates messages are received and transmitted. A receiving message filter control 206 that directs a user to message receiving user interface 130 of FIG. 4. A new transmitting message control 208 that directs a user to message transmitting user interface 160 of FIG. 5.

User interface 200 is shown as including optional summary information 210 indicating numeric summaries of the numbers of users associated with personalized health communication computer system 100 that have indicated health conditions indicated by predefined conditions controls 144, general characteristics controls 146 of message receiving user interface 130, for example. Additionally, user interface 200 is also shown as including a user-defined health condition search control 212—by which a user may conduct a search to obtain a numeric summary of the numbers of users associated with personalized health communication computer system 100 having one or more user-defined health conditions. User-defined health condition search control 212 operates with health terminology thesaurus 108 of personalized health communication server 106, as do the operations involving user-defined health conditions described above.

Having described and illustrated the principles of our invention with reference to an illustrated embodiment, it will be recognized that the illustrated embodiment can be modified in arrangement and detail without departing from such principles. It should be understood that the programs, processes, or methods described herein are not related or limited to any particular type of computer apparatus, unless indicated otherwise. Various types of general purpose or specialized computer apparatus may be used with or perform operations in accordance with the teachings described herein. Elements of the illustrated embodiment shown in software may be implemented in hardware and vice versa.

In view of the many possible embodiments to which the principles of our invention may be applied, it should be recognized that the detailed embodiments are illustrative only and should not be taken as limiting the scope of our invention. Rather, we claim as our invention all such embodiments as may come within the scope and spirit of the following claims and equivalents thereto.

The invention claimed is:

1. A computer-implemented communication method comprising:

from each of a plurality of receiving users, receiving by a computer system corresponding personal health message receiving criteria for determining messages to be received by that receiving user via at least one of e-mail and a personal homepage, the corresponding personal health message receiving criteria for each user including at least one of a personal characteristic, a predefined health condition, and a receiving user-defined health condition that is relevant to that receiving user;

from a transmitting user, receiving a plurality of messages intended for at least one of the receiving users, wherein each message includes i) personal health message transmitting criteria selected by the transmitting user for directing each received message to other users, the personal health message transmitting criteria including at least one of a personal characteristic, a predefined health condition, and a transmitting user-defined health condition that is relevant to at least one of each received message and the transmitting user, and ii) a communication for at least one of the receiving users, wherein each of the plurality of messages is generated by the transmitting user from a transmitting user interface displayed on a display that includes at least one field allowing the transmitting user to select the personal health message transmitting criteria and at least one field to compose the communication;

comparing, by the computer system, the transmitting criteria in each of the plurality of received messages to the personal health message receiving criteria for each of the plurality of receiving users to identify matches; and transmitting each of the plurality of received messages to identified receiving users comprising at least one of the receiving users via at least one of an e-mail and the personal homepage without identifying the identified receiving users to the transmitting user, the transmitting being based on a match between the transmitting criteria and the receiving criteria.

2. The method of claim 1 in which the identified receiving users include those for whom the personal health message receiving criteria include all of the personal health message transmitting criteria.

3. The method of claim 1 in which the identified receiving users include those for whom the personal health message receiving criteria include at least selected ones of the personal health message transmitting criteria.

4. The method of claim 1 wherein receiving corresponding personal health message receiving criteria from each of the plurality of receiving users includes receiving the receiving user-defined health condition that is relevant to that receiving user, the method further including correlating the receiving user-defined health condition with a health terminology thesaurus having concept unique identifiers that correspond to and provide uniform characterizations of the receiving user-defined health condition.

5. The method of claim 1 wherein receiving personal health message transmitting criteria includes receiving the transmitting user-defined health condition that is relevant to at least one of each received message and the transmitting user, the method further including correlating the transmitting user-defined health condition with a health terminology thesaurus.

6. The method of claim 1 further comprising obtaining from each of the plurality of receiving users and the transmitting user corresponding personal health-related information, the health-related information including one or more health-related terms that each corresponds to a health-related concept; and correlating with a health terminology thesaurus each of the one or more health-related terms with a single concept unique identifier that uniquely identifies a corresponding health-related concept, each concept unique identifier having associated with it one or more terms corresponding to a common health-related concept, at least one of the terms being a lay medical term and not a clinical medical term.

7. The method of claim 6 in which computer implementation of the method employs a client computer and a server computer that are interconnected by a computer network, the method further comprising:

transmitting at least some of the corresponding personal health-related information over the computer network from the client computer to the server computer, the server computer storing the health terminology thesaurus; and correlating, by the server computer, each of the one or more health-related terms with a single concept unique identifier.

8. A non-transitory computer-readable medium comprising computer executable instructions that, when executed by a computer, cause the computer to:

receive from each of a plurality of receiving users corresponding personal health message receiving criteria for determining messages to be received by that receiving user via at least one of e-mail and a personal homepage, the corresponding personal health message receiving criteria for each user including at least one of a personal characteristic, a predefined health condition, and a receiving user-defined health condition that is relevant to that receiving user;

receive from a transmitting user a plurality of messages intended for at least one of the receiving users, wherein each message includes i) personal health message transmitting criteria selected by the transmitting user for directing each received message to other users, the personal health message transmitting criteria including at least one of a personal characteristic, a predefined health condition, and a transmitting user-defined health condition that is relevant to at least one of each received message and the transmitting user, and ii) a communication for at least one of the receiving users, wherein each of the plurality of messages is generated by the transmitting user from a transmitting user interface displayed on a display that includes at least one field allowing the transmitting user to select the personal health message transmitting criteria and at least one field to compose the communication;

compare the transmitting criteria in each of the plurality of received messages to the personal health message receiving criteria for each of the plurality of receiving users to identify matches; and transmit each of the plurality of received messages to identified receiving users comprising at least one of the receiving users via at least one of an e-mail and the personal homepage without identifying the identified receiving users to the transmitting user, the transmitting being based on a match between the transmitting criteria and the receiving criteria.

9. The non-transitory computer readable medium of claim 8, wherein the identified receiving users include those for whom the personal health message receiving criteria include all of the personal health message transmitting criteria.

10. The non-transitory computer readable medium of claim 8, wherein the identified receiving users include those for whom the personal health message receiving criteria include at least selected ones of the personal health message transmitting criteria.

11. The non-transitory computer readable medium of claim 8, wherein each of the plurality of receiving users' corresponding personal health message receiving criteria is received using a receiving user interface.

12. The non-transitory computer readable medium of claim 8, wherein each of the plurality of receiving users' corresponding personal health message receiving criteria is received using a receiving user interface that allows the receiving user to identify the receiving user-defined health condition that is relevant to that receiving user, and the computer executable instructions further including instructions that cause the computer to correlate the receiving user-defined health condition with a health terminology thesaurus having concept unique identifiers that correspond to and provide uniform characterizations of the receiving user-defined health condition.

13. The non-transitory computer readable medium of claim 8, wherein the at least one field allowing the transmitting user to select the personal health message transmitting criteria allows the transmitting user to select, for each of the messages, the transmitting user predefined health condition that is relevant to at least one of each received message and the transmitting user from among a predefined set of predefined health conditions.

14. The non-transitory computer readable medium of claim 8, wherein the at least one field allowing the transmitting user to select the personal health message transmitting criteria allows the transmitting user to identify, for each of the messages, the transmitting user-defined health condition that is relevant to at least one of each received message and the transmitting user, the computer executable instructions further including instructions that cause the computer to correlate the transmitting user-defined health condition with a health terminology thesaurus.

15. The non-transitory computer readable medium of claim 8, wherein the instructions are further configured to cause the computer to:
    obtain from each of the plurality of receiving users and the transmitting user corresponding personal health-related information, the health-related information including one or more health-related terms that each corresponds to a health-related concept; and
    correlate with a health terminology thesaurus each of the one or more health-related terms with a single concept unique identifier that uniquely identifies a corresponding health-related concept, each concept unique identifier having associated with it one or more terms corresponding to a common health related concept, at least one of the terms being a lay medical term and not a clinical medical term.

16. The non-transitory computer readable medium of claim 15 in which the instructions are configured such that the computer employs a client computer and a server computer that are interconnected by a computer network, the instructions being further configured to cause the computer to:
    transmit the corresponding personal health-related information over the computer network from the client computer to the server computer, the server computer storing the health terminology thesaurus; and
    correlate, by the server computer, each of the one or more health-related terms with a single concept unique identifier.

17. The method of claim 1, wherein:
    the personal characteristic for the personal health message receiving criteria includes at least one of a gender, an age, an age range, a smoking habit, a non-smoking habit, an exercising habit, a non-exercising habit, an overweight indicator, and an underweight indicator, and
    the personal characteristic for the personal health message transmitting criteria includes at least one of a gender, an age, an age range, a smoking habit, a non-smoking habit, an exercising habit, a non-exercising habit, an overweight indicator and an underweight indicator.

18. The non-transitory computer readable medium of claim 8, wherein:
    the personal characteristic for the personal health message receiving criteria includes at least one of a gender, an age, an age range, a smoking habit, a non-smoking habit, an exercising habit, a non-exercising habit, an overweight indicator and an underweight indicator, and
    the personal characteristic for the personal health message transmitting criteria includes at least one of a gender, an age, an age range, a smoking habit, a non-smoking habit, an exercising habit, a non-exercising habit, an overweight indicator and an underweight indicator.

19. The method of claim 1, wherein
    the predefined health condition for the personal health message receiving criteria includes at least one of pregnancy, high blood pressure, elevated cholesterol, heart disease, Type I diabetes, Type II diabetes, breast cancer, prostate cancer, and colon cancer, and
    the predefined health condition for the personal health message transmitting criteria includes at least one of pregnancy, high blood pressure, elevated cholesterol, heart disease, Type I diabetes, Type II diabetes, breast cancer, prostate cancer, and colon cancer.

20. The non-transitory computer readable medium of claim 8, wherein:
    the predefined health condition for the personal health message receiving criteria includes at least one of pregnancy, high blood pressure, elevated cholesterol, heart disease, Type I diabetes, Type II diabetes, breast cancer, prostate cancer, and colon cancer, and
    the predefined health condition for the personal health message transmitting criteria includes at least one of pregnancy, high blood pressure, elevated cholesterol, heart disease, Type I diabetes, Type II diabetes, breast cancer, prostate cancer, and colon cancer.

* * * * *